US010869827B2

(12) United States Patent
Angel et al.

(10) Patent No.: US 10,869,827 B2
(45) Date of Patent: Dec. 22, 2020

(54) COMPOSITIONS AND KITS FOR THE REMOVAL OF IRRITATING COMPOUNDS FROM BODILY SURFACES

(71) Applicant: Averitas Pharma Inc., Morristown, NJ (US)

(72) Inventors: Arturo J. Angel, Santa Rosa, CA (US); Larry W. Litle, Lee's Summit, MO (US); Keith R. Bley, Menlo Park, CA (US); Allan L. Wilcox, Mountain View, CA (US); Gene C. Jamieson, Boulder Creek, CA (US); Naweed Muhammad, Fremont, CA (US)

(73) Assignee: Averitas Pharma Inc., Morristown, NJ (US)

( * ) Notice: Subject to any disclaimer, the term of this patent is extended or adjusted under 35 U.S.C. 154(b) by 0 days.

(21) Appl. No.: 16/581,102

(22) Filed: Sep. 24, 2019

(65) Prior Publication Data

US 2020/0085718 A1     Mar. 19, 2020

Related U.S. Application Data

(60) Division of application No. 15/377,804, filed on Dec. 13, 2016, now Pat. No. 10,463,598, which is a
(Continued)

(51) Int. Cl.
*A61K 8/86*     (2006.01)
*A61K 31/16*     (2006.01)
(Continued)

(52) U.S. Cl.
CPC .................. *A61K 8/86* (2013.01); *A61K 8/33* (2013.01); *A61K 8/42* (2013.01); *A61K 8/44* (2013.01);
(Continued)

(58) Field of Classification Search
CPC ........ A61K 31/16; A61K 31/165; A61K 9/70; A61K 9/7023; A61K 8/042; A61K 8/86;
(Continued)

(56) References Cited

U.S. PATENT DOCUMENTS 4,303,066 A    12/1981   D'Andrea
4,387,107 A     6/1983   Klein et al.
(Continued)

FOREIGN PATENT DOCUMENTS

DE        3038604 A1    5/1982
EP         0 228 868      7/1987
(Continued)

OTHER PUBLICATIONS

Allen, L.V. (Nov. 1998). "Coumarin: Agent With Many Uses," U.S. Pharm. 23:106-108.
(Continued)

*Primary Examiner* — Lakshmi S Channavajjala
(74) *Attorney, Agent, or Firm* — Morrison & Foerster LLP

(57) ABSTRACT

The invention provides compositions, methods and kits for the removal of harmful or irritating substances from bodily surfaces. Kits may include a composition containing capsaicin and a capsaicin-cleansing composition, e.g., a composition in which capsaicin is soluble.

24 Claims, 1 Drawing Sheet

Related U.S. Application Data division of application No. 14/542,041, filed on Nov. 14, 2014, now Pat. No. 9,549,893, which is a continuation of application No. 13/596,773, filed on Aug. 28, 2012, now Pat. No. 8,889,113, which is a continuation of application No. 12/830,997, filed on Jul. 6, 2010, now Pat. No. 8,263,059, which is a continuation of application No. 10/655,911, filed on Sep. 5, 2003, now abandoned.

(60) Provisional application No. 60/410,616, filed on Sep. 13, 2002, provisional application No. 60/408,751, filed on Sep. 5, 2002.

(51) Int. Cl.
| | |
|---|---|
| *A61K 8/42* | (2006.01) |
| *A61Q 17/00* | (2006.01) |
| *A61Q 19/10* | (2006.01) |
| *A61K 9/00* | (2006.01) |
| *A61K 8/33* | (2006.01) |
| *A61K 8/44* | (2006.01) |
| *A61K 8/81* | (2006.01) |
| *A61K 9/70* | (2006.01) |
| *A61K 31/165* | (2006.01) |

(52) U.S. Cl.
CPC .......... *A61K 8/8152* (2013.01); *A61K 9/0014* (2013.01); *A61K 9/7084* (2013.01); *A61K 31/16* (2013.01); *A61K 31/165* (2013.01); *A61Q 17/00* (2013.01); *A61Q 19/10* (2013.01); *A61K 2800/75* (2013.01); *A61K 2800/88* (2013.01)

(58) Field of Classification Search
CPC .... A61K 8/8152; A61K 8/8164; A61Q 17/00; A61Q 19/10
See application file for complete search history.

(56) References Cited

U.S. PATENT DOCUMENTS

| | | |
|---|---|---|
| 4,393,076 A | 7/1983 | Noda et al. |
| 4,424,205 A | 1/1984 | LaHann et al. |
| 4,493,848 A | 1/1985 | LaHann et al. |
| 4,599,379 A | 7/1986 | Flesher et al. |
| 4,628,078 A | 12/1986 | Glover et al. |
| 4,812,446 A | 3/1989 | Brand |
| 4,835,206 A | 5/1989 | Farrar et al. |
| 4,849,484 A | 7/1989 | Heard |
| 4,911,933 A | 3/1990 | Gilbard |
| 5,100,660 A | 3/1992 | Hawe et al. |
| 5,202,118 A | 4/1993 | Gillis et al. |
| 5,288,814 A | 2/1994 | Long, II et al. |
| 5,290,816 A | 3/1994 | Blumberg |
| 5,468,814 A | 11/1995 | Stover et al. |
| 5,523,017 A | 6/1996 | Moran et al. |
| 5,624,906 A | 4/1997 | Vermeer |
| 5,633,285 A | 5/1997 | Martin |
| 5,698,191 A | 12/1997 | Wiersma et al. |
| 5,703,026 A | 12/1997 | Setser et al. |
| 5,721,275 A | 2/1998 | Bazzano |
| 5,747,052 A | 5/1998 | Mimikos et al. |
| 5,827,886 A | 10/1998 | Hersh |
| 5,856,361 A | 1/1999 | Holt et al. |
| 5,910,512 A | 6/1999 | Conant |
| 5,922,331 A | 7/1999 | Mausner |
| 5,958,436 A | 9/1999 | Hahn et al. |
| 5,962,532 A | 10/1999 | Campbell et al. |
| 5,994,407 A | 11/1999 | Cuilty-Siller |
| 6,013,270 A | 1/2000 | Hargraves et al. |
| 6,015,763 A | 1/2000 | Vlasblom |
| 6,113,892 A | 9/2000 | Newell et al. |
| 6,114,290 A | 9/2000 | Lyle et al. |
| 6,133,212 A | 10/2000 | Elliott et al. |
| 6,203,804 B1 | 3/2001 | Murakado et al. |
| 6,239,180 B1 | 5/2001 | Robbins |
| 6,248,788 B1 | 6/2001 | Robbins et al. |
| 6,277,385 B1 | 8/2001 | Luke |
| 6,342,470 B1 | 1/2002 | Aronson |
| 6,390,291 B1 | 5/2002 | Garrill et al. |
| 6,403,589 B1 | 6/2002 | Meert et al. |
| 6,428,772 B1 | 8/2002 | Singh et al. |
| 6,569,463 B2 | 5/2003 | Patel et al. |
| 6,593,370 B2 | 7/2003 | Tamura et al. |
| 6,641,825 B2 | 11/2003 | Scholz et al. |
| 7,074,747 B1 | 7/2006 | Lukenbach et al. |
| 7,262,158 B1 | 8/2007 | Lukenbach et al. |
| 8,263,059 B2 | 9/2012 | Angel et al. |
| 8,889,113 B2 | 11/2014 | Angel et al. |
| 9,549,893 B2 | 1/2017 | Angel et al. |
| 2001/0002406 A1 | 5/2001 | Robbins |
| 2003/0235549 A1 | 12/2003 | Singh et al. |
| 2004/0126430 A1 | 7/2004 | Angel et al. |
| 2004/0180081 A1 | 9/2004 | Angel et al. |
| 2006/0188454 A1 | 8/2006 | Corcoran et al. |
| 2006/0204563 A1 | 9/2006 | Angel et al. |
| 2006/0204564 A1 | 9/2006 | Angel et al. |
| 2017/0312214 A1 | 11/2017 | Angel et al. |

FOREIGN PATENT DOCUMENTS

| | | |
|---|---|---|
| EP | 2 721 213 B1 | 12/1995 |
| EP | 0 916 334 A1 | 5/1999 |
| EP | 1 016 403 A2 | 7/2000 |
| EP | 1 016 403 A3 | 7/2000 |
| FR | 2 721 213 A1 | 12/1995 |
| WO | WO-01/07096 A1 | 2/2001 |
| WO | WO-02/45662 A2 | 6/2002 |
| WO | WO-02/45662 A3 | 6/2002 |
| WO | WO-02/102398 A1 | 12/2002 |
| WO | WO-2004/021990 A1 | 3/2004 |
| WO | WO-2005/027642 A1 | 3/2005 |

OTHER PUBLICATIONS

Amjad, Z. et al. (1992). "Carbomer Resins: Past, Present and Future," Cosmetics & Toiletries 107:81-85.

Anonymous. (2000). Capsaicin Data Sheet located at Wholehealthmd.com, 4 pages.

British Industrial Biological Research Association. (1991). "Toxicity Profile: Polyethylene Glycol 300 (PEG 300)," British Industrial Biological Research Association Government Reports Announcements and Index, 19:1-5.

Brown, V.K.H. et al. (1975). "Decontamination Procedures for Skin Exposed to Phenolic Substances," Arch. Environ Health 30:1-6.

Convert Pa-s to centipoise conversion of measurements units. Printed Nov. 26, 2018. https://www.convertunits.com/from/Pa-s/to/centipoise. 2 pages.

Edlich, R.F. et al. (Nov. 6, 2003). "Burns, Chemical" located at <http://www.emedicine.com/plastic/topic 492.html> last visited on Jul. 6, 2004, 17 pages.

Govindarajan, V.S. et al. (1991). "Capsium—Production, Technology, Chemistry, and Quality. Part V. Impact on Physiology, Pharmacology, Nutrition, and Metabolism; Structure, Pungency, Pain, and Desensitization Sequences," Food Science and Nutrition 29:435-474.

Hemker, W. (Nov. 1991). "Universal oil-in-water Polyelectrolyte Emulsifiers for Advanced Cosmetic Product Formulation," Parfümerie and Kosmetik. 72:730-741.

Jones, L. A. et al. (Nov. 1987). "Household Treatment for Chile Burns on Hands," Clinical Toxicology 25(6):483-491, Abstract Only.

Knezevic, D.L. et al. (1992). "Efficacy of Different Formulations of Protective Ointments in Animals Percutaneously Poisoned With Highly Toxic Organophosphates," Arh. Farm. 42(4-5):119-126.

Laws, R. et al. (Nov. 12, 2002). "Burns, Chemical" located at <http://www.emedicine.com/derm/topic777.html> last visited on Jul. 6, 2004, 14 pages.

(56) References Cited

OTHER PUBLICATIONS

Leber, A.P. et al. (1990). "Triethylene Glycol Ethers: Evaluations of In Vitro Absorption Through Human Epidermis, 21-Day Dermal Toxicity in Rabbits, and a Developmental Toxicity Screen in Rats," J. Am. Coll. Toxicol. 9(5):507-515.

Lee, D.C. et al. (Jun., 2003). "Magnesium-Aluminum Hydroxide Suspension for the Treatment of Dermal Capsaicin Exposures," Acad. Emerg. Med. 10(6):688-690.

Lochhead, R.Y. et al. eds. (1993). "Encyclopedia of Polymers and Thickners," Cosmetics & Toiletries 108:95-135.

Miller, C.H. (1994). "Inhibition of NNK Mutagenesis and Metabolism by Chemopreventive Phytochemicals (Tobacco, Nitrosamines)," Abstract, Diss. Abstr. Int. (B) 55(6):2219.

Olson, C.T. et al. (1991). "Evaluation of Compounds as Barriers to Dermal Penetration of Organophosphates Using Acetylcholinesterase Inhibition," Toxicology Letters 55:325-334.

Osol, A. et al. eds. (1975). Remington's Pharmaceutical Sciences 15th Edition, Mack Publishing Co.: Easton, PA p. xi (Table of Contents Only.).

Pullin, T.G. et al. (1978). "Decontamination of the Skin of Swine Following Phenol Exposure: A Comparison of the Relative Efficacy of Water Versus Polyethylene Glycol/Industrial Methylated Spirits," Toxicology and Applied Pharmacology 43:199-206.

Roberts, M.S. et al. (1977). "Permeability of Human Epidermis to Phenolic Compounds," J. Pharm. Pharmacol. 29:677-683.

Roberts, M.S. et al. (1978). "The Percutaneous Absorption of Phenolic Compounds: The Mechanism of Diffusion Across the Stratum Corneum," J. Pharm. Pharmacol. 30:486-490.

Toh, C.C. et al. (1955). "The Pharmacological Actions of Capsaicin and Analogues," Brit. J. Pharmacol. 10:175-182.

United States Pharmacopeial Convention, Inc. eds. (1999). USP24/ NF19 U.S. Pharmcopeia/National Formulary United States Pharmacopeial Convention, Inc. Meeting at Washington, DC (Mar. 9-12, 1995) p. 2405.

Watson, H.R. et al. (1978). "New Compounds with the Menthol Cooling Effect," J. Soc. Cosmet. Chem. 29:185-200.

Wenninger, J.A. et al. eds. (1997). International Cosmetic Ingredient Dictionary and Handbook, Seventh Edition, The Cosmetic, Toiletry, and Fragrance Association: Washington, DC vol. 1-3, (Table of Contents Only.).

Wenninger, J.A. et al. eds. (2000). International Cosmetic Ingredient Dictionary and Handbook, Eighth Edition, The Cosmetic, Toiletry, and Fragrance Association: Washington, DC vol. 1-3, (Table of Contents Only.).

Zatz, J.L. et al. (Sep.-Oct. 1983). "Evaluation of Solvent-Skin Interaction in Percutaneous Absorption," J. Soc. Cosmet. Chem. 34:327-334.

International Search Report dated Jun. 30, 2004, for PCT Patent Application No. PCT/US03/27742 filed on Sep. 5, 2003, 6 pages.

Supplementary European Search Report dated Jan. 24, 2011, for EP Patent Application No. 03752011.1, filed on Sep. 5, 2003, 3 pages.

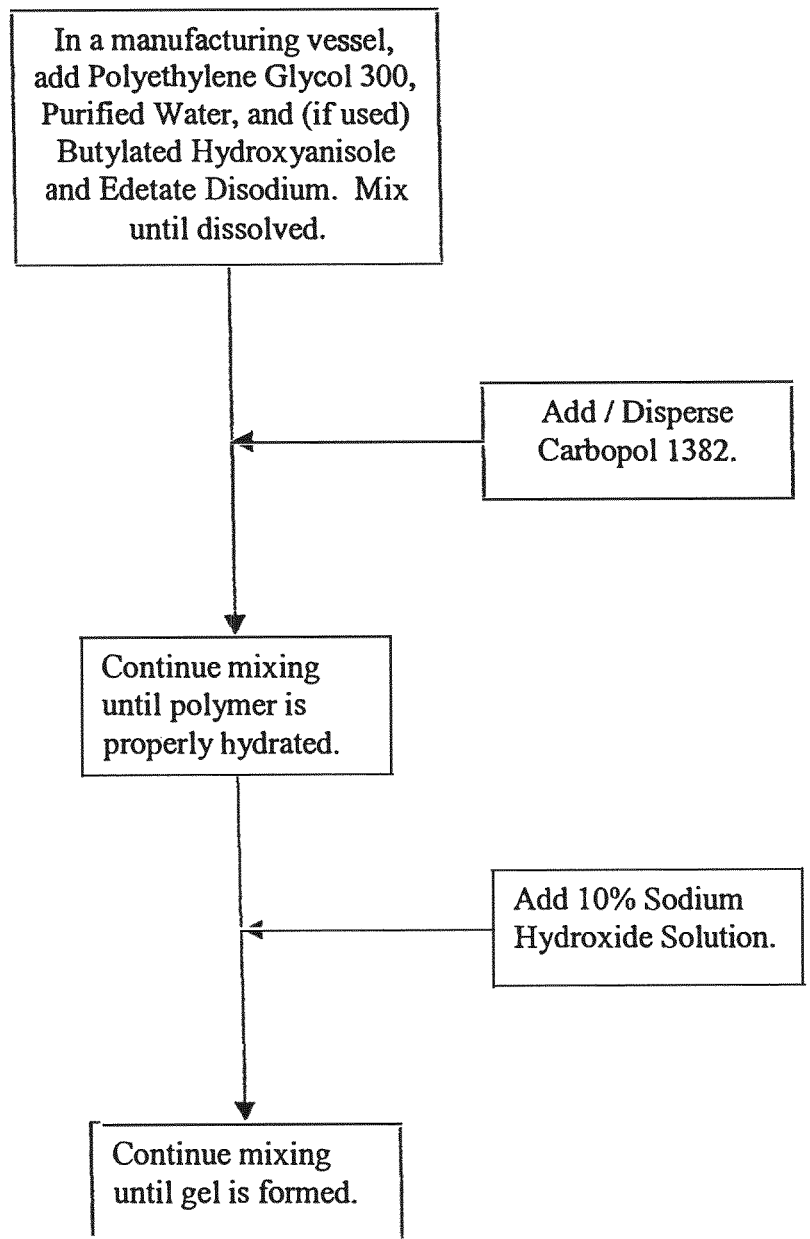

COMPOSITIONS AND KITS FOR THE REMOVAL OF IRRITATING COMPOUNDS FROM BODILY SURFACES

CROSS-REFERENCE TO RELATED APPLICATIONS

This application is a divisional application of U.S. application Ser. No. 15/377,804, filed on Dec. 13, 2016, which is a divisional application of U.S. application Ser. No. 14/542,041, filed on Nov. 14, 2014, now U.S. Pat. No. 9,549,893, which is a continuation of U.S. application Ser. No. 13/596,773, filed on Aug. 28, 2012, now U.S. Pat. No. 8,889,113 which is a continuation of U.S. application Ser. No. 12/830,997, filed on Jul. 6, 2010, now U.S. Pat. No. 8,263,059, which is a continuation of U.S. application Ser. No. 10/655,911, filed Sep. 5, 2003, now abandoned, which claims the benefit of U.S. Provisional Patent Application Nos. 60/408,751, filed Sep. 5, 2002, and 60/410,616, filed Sep. 13, 2002, the disclosures of each of which is hereby incorporated by reference in their entirety.

TECHNICAL FIELD

The invention relates to kits, compositions, and methods for the removal of harmful or irritating substances from bodily surfaces, in particular to kits containing a composition containing capsaicin or a capsaicin analog and a capsaicin-cleansing composition. Such kits and compositions find application in medicine and animal health.

BACKGROUND OF THE INVENTION

Many compounds are irritating or painful when contacted with bodily surfaces.

Examples include urushiols, which are constituents of poison oak, poison ivy, poison sumac, and other oily plant resins with irritating properties. Another example is capsaicin. Capsaicin is a constituent of pepper sprays, and capsaicin and its analogs are used in topical form for pain relief. Even at low concentrations (e.g., 0.075% by weight) capsaicin preparations can cause burning pain and hyperalgesia. This is the effect sought in pepper sprays, and is a side effect of therapeutic treatments of pain. At higher capsaicin concentrations used for the treatment of some intractable pain conditions, the initial pain accompanying application of capsaicin is treated by anesthesia (see, e.g., U.S. Pat. Nos. 6,248,788 and 6,239,180).

BRIEF SUMMARY OF THE INVENTION

One aspect of the invention provides a kit that includes a first device or composition containing capsaicin or a capsaicin analog; and a second device or composition containing a substance in which capsaicin is soluble, wherein the first and second devices or compositions are separately packaged. In some embodiments, the second composition is a composition in which capsaicin has a solubility of at least about 10 percent w/w. In some embodiments, the second composition is a composition in which capsaicin has a solubility of at least about 20 percent w/w. In some embodiments, the second composition is a composition in which capsaicin has a solubility of at least about 25 percent w/w. The compositions are useful for effectively removing capsaicin and other irritating or painful resinous or oily substances from bodily surfaces quickly and effectively in order to minimize pain and irritation from the substances. In certain embodiments, the first composition of the kit may include capsaicin or a capsaicin analog in an amount sufficient to treat a capsaicin-responsive condition (e.g., a therapeutically effective amount), for example, a concentration between about 0.001 to about 60 percent w/w, e.g., about 0.001 to about 1 percent w/w, or about 0.1 to about 15 percent w/w or about 1 to about 10 percent w/w; for example, about 5 to about 10 percent w/w. In some embodiments, the capsaicin or capsaicin analog is contained in a spray, lotion, emulsion, liniment, or gel. In other embodiments, the capsaicin or capsaicin analog is contained in a transdermal patch. In one such embodiment, the capsaicin or capsaicin analog is present in the transdermal patch at an amount of about 0.64 mg/cm$^2$. In some embodiments of this aspect of the invention, the second composition of the kit contains polyethylene glycol and a polyacrylate thickening polymer. In some embodiments, the second composition of the kit contains about 60 to about 99 percent w/w polyethylene glycol (PEG); about 0.1 to about 4.0 percent w/w polyacrylate thickening agent; and the balance water; wherein the composition is at a pH between about 6.0 and about 8.0. In some embodiments, the second composition of the kit contains about 84 to about 94 percent w/w polyethylene glycol; about 0.1 to about 2 percent w/w polyacrylate thickening agent; and the balance water; wherein the composition is at a pH of about 7.0 to 7.5. In further embodiments of this aspect of the invention, the second composition of the kit may contain, in addition to PEG and a polyacrylate thickener, about 0.005 to about 0.05 percent w/w butylated hydroxyanisole; and about 0.05 to about 0.5 percent w/w EDTA/EDTA salts.

In some embodiments, the kit includes a third composition comprising an anesthetic.

Kits of the invention may also include instructions for use of the capsaicin composition and the cleansing composition.

In one aspect, the invention provides a kit comprising a transdermal patch comprising capsaicin and a capsaicin cleansing gel. The kit may also provide an anesthetic. For example, in one embodiment, the transdermal patch contains capsaicin at an amount of about 0.64 mg/cm$^2$; a cleansing gel containing about 84 to about 94 percent w/w polyethylene glycol, about 0.1 to about 2 percent w/w polyacrylate thickening agent, about 0.005 to about 0.05 percent w/w butylated hydroxyanisole, about 0.05 to about 0.5 percent w/w EDTA/EDTA salts, and the balance water; wherein the second composition is at a pH of about 7.0 to 7.7; and a composition comprising an anesthetic. This embodiment may further contain instructions for use.

In another aspect, the present invention provides a composition for cleansing a bodily surface. In embodiments, the invention provides composition in which capsaicin has a solubility of at least about 10% w/w, or at least about 20% w/w, or at least about 25% w/w. Some embodiments of compositions provided by the invention include a component in which capsaicin is soluble, e.g., a component in which capsaicin is soluble to greater than about 10% w/w, greater than about 20% w/w, or greater than about 25% w/w, and a thickening agent. In one embodiment, a composition of the invention contains about 60 to about 99 percent w/w polyethylene glycol (PEG, e.g., PEG 300). In one embodiment, a composition of the invention contains about 60 to about 99 percent w/w polyethylene glycol (PEG, e.g., PEG 300), about 0.1 to about 4 percent w/w thickening agent, and the balance water; wherein the composition is at a pH between about 6.0 and about 8.0. The thickening agent can be a polyacrylate. In another embodiment, the composition includes about 84 to about 94 percent w/w polyethylene glycol (PEG, e.g., PEG 300); about 0.1 to about 2 percent w/w polyacrylate thickening agent; and the balance water; wherein the composition is at a pH between about 7.0 and about 7.7. In a further embodiment, the composition includes about 88 to about 92 percent w/w polyethylene glycol (PEG, e.g., PEG 300); about 0.1 to about 2 percent w/w polyacrylate thickening agent; and the balance water; wherein the composition is at a pH between about 7.0 and about 7.7. In yet a further embodiment, the composition includes about 90 percent w/w polyethylene glycol (PEG, e.g., PEG 300); about 0.1 to about 2 percent w/w polyacrylate thickening agent; and the balance water; wherein the composition is at a pH between about 7.0 and about 7.7. In still another embodiment, the composition includes about 84 to about 94 percent w/w polyethylene glycol (PEG, e.g., PEG 300); about 0.3 to about 1.5 percent w/w polyacrylate thickening agent; and the balance water; wherein the composition is at a pH between about 7.0 and about 7.7. In still yet another embodiment, the composition includes about 84 to about 94 percent w/w polyethylene glycol (PEG, e.g., PEG 300); about 1.0 percent w/w polyacrylate thickening agent; and the balance water; wherein the composition is at a pH between about 7.0 and about 7.7. In some embodiments of the invention, the polyethylene glycol comprises PEG 200 or PEG 300.

Compositions of the invention may also contain, in addition to PEG and a thickening agent, stabilizer(s). In some embodiments, stabilizers of the invention include about 0.005 to about 0.05 percent w/w butylated hydroxyanisole; and about 0.05 to about 0.5 percent w/w EDTA/EDTA salts. Some embodiments that include stabilizers may include about 87 to about 91 percent w/w polyethylene glycol; about 0.3 to about 1.5 percent w/w polyacrylate thickening agent; about 0.01 to about 0.03 percent w/w butylated hydroxyanisole; about 0.02 to about 0.2 percent w/w EDTA/EDTA salts; and the balance water; wherein the composition is at a pH of about 7.0 to about 7.7. A further embodiment includes about 89.08 percent w/w PEG 300; about 1.0 percent w/w polyacrylate thickening agent; about 0.02 percent w/w butylated hydroxyanisole; about 0.1 percent w/w EDTA/EDTA salts; and the balance water; wherein the composition is at a pH of about 7.5.

In another aspect, the invention includes an article of manufacture for cleansing a bodily surface including (a) a composition containing about 84 to about 94 percent w/w polyethylene glycol (PEG); about 0.1 to about 2.0 percent w/w polyacrylate thickening agent; and the balance water; wherein the composition is at a pH between about 7.0 and about 7.7; and (b) a container suitable for dispensing the composition of (a); where either the container is labeled with instructions for the use of the composition of (a), or the article of manufacture includes separate instructions for the use of the composition of (a).

Yet another aspect of the invention includes a method for cleansing a bodily surface that has been contacted with an irritating or painful substance. In some embodiments, the method includes the steps of (a) applying to the bodily surface a composition in which capsaicin has a solubility of at least about 10% w/w, or at least about 20% w/w, or at least about 25% w/w.; and (b) removing the composition of step (a) from the bodily surface. In some embodiments, the method includes the steps of (a) applying to the bodily surface a composition that contains about 60 to about 99 percent w/w polyethylene glycol (PEG, e.g., PEG 300); and (b) removing the composition of step (a) from the bodily surface. In some embodiments, the method includes the steps of (a) applying to the bodily surface a composition that contains about 60 to about 99 percent w/w polyethylene glycol (PEG, e.g., PEG 300), about 0.1 to about 4 percent w/w thickening agent, and the balance water; wherein the composition is at a pH between about 6.0 and about 8.0.; and (b) removing the composition of step (a) from the bodily surface. In some embodiments, the method includes the steps of (a) applying to the bodily surface a composition containing about 80 to about 99 percent w/w polyethylene glycol, about 0.1 to about 2 percent w/w polyacrylate thickening agent and the balance water; wherein the composition is at a pH of about 7.0 to about 7.7; and (b) removing the composition of step (a) from the bodily surface. In other embodiment, the method includes the steps of (a) applying to the bodily surface a composition containing about 87 to about 91 percent w/w polyethylene glycol, about 0.3 to about 1.5 percent w/w polyacrylate thickening agent, about 0.01 to about 0.03 percent w/w butylated hydroxyanisole, about 0.02 to about 0.2 percent w/w EDTA/EDTA salts and the balance water; wherein the composition is at a pH of about 7.0 to about 7.7; and (b) removing the composition of step (a) from the bodily surface.

Yet a further aspect of the invention includes a method for treating an individual suffering from a capsaicin-responsive condition. In one embodiment, the invention provides a method for treating pain in an individual, including the steps of (a) applying a composition containing capsaicin or a capsaicin analog to the painful area; and (b) cleansing bodily surfaces that have been exposed to capsaicin by applying to the bodily surfaces a composition comprising a component in which capsaicin has a solubility of greater than 10% w/w, or greater than 20% w/w, or greater than 25% w/w; and removing said composition from the area. In some embodiments of this aspect of the invention, the capsaicin or capsaicin analog is present in the capsaicin-containing composition in a total concentration greater than about 5% by weight. In some embodiments of this aspect of the invention, step (a) of the method includes affixing to the affected area a skin-adherent patch, the patch including a reservoir containing a therapeutic formulation whereby said formulation is provided to the surface of the skin, and where the formulation contains capsaicin or a capsaicin analog in a total concentration from greater than about 5% to 10% by weight of the formulation. In some embodiments of this aspect of the invention, the method further includes, in addition to applying capsaicin or capsaicin analogs and removing the capsaicin or capsaicin analogs, administering an anesthetic to the individual in whom pain is to be treated, prior to the application of the capsaicin or capsaicin analog. In some of these embodiments, the anesthetic is administered in the form of an afferent nerve block.

BRIEF DESCRIPTION OF THE DRAWING

FIG. 1 illustrates schematically the manufacturing process for a cleansing solution.

DETAILED DESCRIPTION OF THE INVENTION

The invention provides kits that contain a component containing capsaicin or a capsaicin analog, and another component for cleansing capsaicin or a capsaicin analog, and methods for their use. The invention also provides compositions useful for cleansing skin and other bodily surfaces, e.g., eyes and mucous membranes, that have been exposed to painful or irritating compounds, and methods for their use.

In one aspect, the invention provides kits that include a composition containing capsaicin or a capsaicin analog together with a capsaicin cleansing composition in which capsaicin or a capsaicin analog is soluble. In some embodiments, capsaicin or the capsaicin analog is soluble to at least about 10% w/w, at least about 20% w/w, or at least about 25% w/w in the capsaicin cleansing composition. The kits may further include a composition containing an anesthetic, instructions, and other optional components.

In one aspect the invention provides compositions for cleansing skin and other bodily surfaces that have been exposed to a painful or irritating substance, e.g., capsaicin or a capsaicin analog. In embodiments, the invention provides compositions in which capsaicin is soluble, e.g., in which capsaicin has a high solubility, that are non-toxic, and that are easy to apply and to remove. In an embodiment, the compositions do not readily penetrate the skin. In some embodiments the compositions contain polyethylene glycol, a polyacrylate thickening agent, and water, at a pH suitable for topical use. In some embodiments, the compositions may also contain preservatives such as an antioxidant and a chelating agent. The compositions may be applied to bodily surfaces exposed to capsaicin or other painful or irritating compounds, e.g., by a tissue impregnated with the composition, then wiped off the bodily surface, to neutralize the irritating effect of the compound, e.g., capsaicin, on the eyes, skin, fascia, and mucous membranes.

In a further aspect, the invention provides methods for removing irritating or painful substances from bodily surfaces by applying the compositions of the invention to the bodily surface, then removing them. In a yet further aspect, the invention provides methods for treating a capsaicin-responsive condition by applying capsaicin or a capsaicin analog to a bodily surface, then removing excess capsaicin or capsaicin analog. In some of these embodiments, the capsaicin-responsive condition is pain.

All percentages and ratios used herein are by weight of the total composition (i.e., w/w), and all measurements made are at 25° C., unless otherwise designated.

I. Compositions

Compositions provided herein include a first component in which capsaicin and its analogs are soluble, e.g., have high solubility. In some embodiments the compositions include a second component that acts as a thickening agent, and water. If necessary, the pH is modified by a suitable pH modifier to a range appropriate for application to bodily surfaces, i.e., non-harmful and non-irritating pH. In some embodiments the composition also includes stabilizers and/or other components. In some embodiments, the composition contains polyethylene glycol at high concentration and CARBOPOL 1382™ or similar carbomer or thickening agent, optionally including BHA and EDTA/EDTA salts. In some embodiments, the compositions contain polyethylene glycol, a polyacrylate thickener, and water, and are substantially free of other components.

In some embodiments of the invention, the cleansing composition is substantially free of surfactant and/or particulates. By "substantially free" is meant that no surfactant and/or particulate is added to the composition, and any such components are present, if at all, only as trace impurities. These embodiments particularly lend themselves to removal of capsaicin from exposed bodily surfaces, because the surface is already extremely sensitive due to a pre-existing medical condition and any additional irritation from particulate, surfactant, or other additives is undesirable. Surprisingly, despite the lack of particulates and surfactant to assist in reaching irregularities of the skin and to assist in cleansing oily components, the compositions of the invention thoroughly cleanse bodily surfaces of capsaicin. The compositions of the invention may also be used for removal of other agents from bodily surfaces, e.g., toxins (e.g., pesticides, animal toxins), household chemicals (e.g., paint, varnish), and the like. As shown in Example 6, components of the cleansing solution typically do not penetrate the stratum corneum. For illustration and not limitation, various aspects of the compositions will be described in greater detail.

A. Capsaicin-Solubilizing Agent

Provided are compositions that can be applied to a bodily surface that has been exposed to an irritating or painful substance. These compositions may be described herein as "cleansing compositions" and, when the irritating or painful substance is capsaicin, "capsaicin-cleansing compositions." As used herein, a composition "cleanses" a bodily surface of a painful or irritating substance, or is a "cleansing composition," if, when the composition is applied to a bodily surface that has been exposed to a painful or irritating substance, then removed from the bodily surface, a substantial portion of the painful or irritating substance is also removed from the bodily surface. Without being bound by theory, compositions may cleanse a bodily surface when, on application to the exposed bodily surface, the composition acts to dissolve or mix with the irritating or painful substance without significantly penetrating the skin or other bodily surface, and can then be removed from the bodily surface, thereby removing a substantial portion of the painful or irritating substance.

In one aspect, the invention comprises compositions containing a component in which capsaicin or an analog of capsaicin is soluble; in some embodiments, the component is one in which capsaicin has a high solubility (i.e., greater than 10% w/w, or greater than 20% w/w, greater than 25% w/w). Nonlimiting examples of substances in which capsaicin or its analogs may have a high solubility include lower monovalent alcohols (e.g., $C_1$-$C_4$) and low molecular weight glycols and polyols, including propylene glycol, polyethylene glycol (e.g., 200-600 g/mole), polypropylene glycol (e.g., 425-2025 g/mole), glycerol, butylene glycol, 1,2,4-butanetriol, sorbitol esters, 1,2,6-hexanetriol, ethanol, isopropanol, butanediol, ether propanol, ethoxylated ethers, propoxylated ethers and combinations thereof.

In one embodiment the component in which capsaicin has a high solubility is polyethylene glycol (PEG). Polyethylene glycol is an addition polymer of ethylene oxide and water, represented by the formula:

where n represents the average number of oxyethylene groups. There is a wide variety of PEGs and derivatives thereof, and the choice of PEG, PEGs, or their derivatives to be used in the lotions of the invention is mainly driven by considerations of viscosity; the desired viscosity depends on the type of lotion, gel, cream, liniment, or spray to be formulated (see section on viscosity). Hence, suitable PEG's useful in embodiments of the invention include, for example, PEG 200-600. In some embodiments of the invention, PEG 300 is used. PEG 300 has an average molecular weight of 300 and average n=6. Other PEGs may be used in embodiments of the invention. Non-limiting examples include PEG 200 and PEG 400. PEG may be used that is substantially free of ethanol and/or methanol. PEG (e.g., PEG 300) may be provided in the compositions at a concentration of, e.g., about 60 to about 99.9 percent w/w, or about 80 to about 95 percent w/w, or about 84 to about 94 percent w/w, or about 87 to about 91 percent w/w, or about 89 percent w/w. Surprisingly, it was found that PEG 300 at 90% w/w in water retains almost the same solubility for capsaicin as pure PEG 300 (27.0% v. 27.5% solubility of capsaicin, respectively, see Example 2).

B. Thickener

Suitable thickeners for use in the compositions of the present invention include crosslinked polyacrylate polymers, carboxylic acid polymers, polyacrylamide polymers, and mixtures thereof. Exemplary thickeners are polymeric thickening agents including acrylic acid/ethyl acrylate copolymers and the carboxyvinyl polymers sold by the B.F. Goodrich Company under the trade mark of CARBOPOL resins. Such resins are described in, e.g., U.S. Pat. Nos. 5,288,814 and 5,468,814, and in Amjad et al., Carbomer Resins: Past, Present and Future Cosmetics & Toiletries 107 (1992), pp 81-85. These resins consist essentially of a colloidally water-soluble polyalkenyl polyether crosslinked polymer of acrylic acid crosslinked with from 0.75% to 2.00% of a crosslinking agent such as for example polyallyl sucrose or polyallyl pentaerythritol. Examples include Carbopol 934, Carbopol 940, Carbopol 950, Carbopol 980, Carbopol 951 and Carbopol 981. Also suitable for use herein are hydrophobically-modified cross-linked polymers of acrylic acid having amphipathic properties available under the Trade Name Carbopol 1382, Carbopol 1342 and Pemulen TR-1 (CFTA Designation: Acrylates/10-30 Alkyl Acrylate Crosspolymer). Carbopol 1382 is an exemplary CARBOPOL polymer that is used in some embodiments of the invention. See, e.g., U.S. Pat. No. 6,133,212. Other useful crosslinked nonionic polyacrylate polymers and crosslinked cationic polyacrylate polymers are described in U.S. Pat. Nos. 5,100,660; 4,849,484; 4,835,206; 4,628,078; 4,599,379; and EP 228,868, to Farrar et al, published Jul. 15, 1987.

Other thickeners may also be used in the invention, and include acacia, agar, alginic acid, aluminum monostearate, attapulgite (activated or colloidal activated), bentonite, purified bentonite, bentonite magma, carbomers 910, 934, 934P, 940, 941, and/or 1342, carboxymethylcellulose calcium, carboxymethylcellulose sodium, carboxymethylcellulose sodium 12, carrageenan, microcrystalline cellulose, dextrin, gelatin, guar gum, hyaluronic acid, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum, aluminum silicates, and other thickeners known in the art; see, e.g., U.S. Pat. No. 4,387,107, Lochhead et al., Cosmetics & Toiletries 108:95-135 (1993), and USP24/NF19 U.S. Pharmcopeia/National Formulary, p. 2405 (1999).

The thickener is present in a concentration sufficient to provide proper viscosity to the composition for easy application to and removal from skin and other bodily surfaces. The viscosity provided by the thickener, in combination with the polyethylene glycol, water, and optionally other components of the composition, may be in the range from, e.g., a minimum of about 100, or about 300, or about 700, or about 2000, or about 4000 centipoise (cps) to a maximum of about 500, or about 700, or about 1000, or about 5000, or about 8000 cps. The desired viscosity depends on the type of application. In some embodiments the composition comprises a lotion to be applied by wiping and/or rubbing, which is preferably of a viscosity of about 4000 to about 8000 cps. In other embodiments the composition comprises a less viscous preparation that may be applied by spraying, which is preferably of a viscosity of about 100 to about 1000 cps. Other embodiments of intermediate viscosity between spray and lotion can also be useful. The percentage of thickener in the composition depends on the type of PEG used (e.g., PEG 200, 300, or 400) and the percentage of PEG. The quantity of carbomer to be used is determined by the desired viscosity which in turn depends on the intrinsic viscosity of carbomer. The intrinsic viscosity depends on ionic strength, pH, and electrolyte type present. In some embodiments, a polyacrylate polymer, for example CARBOPOL 1382™ comprises, e.g., about 0.1 to about 8 percent w/w, or about 0.1 to about 2 percent w/w, or about 0.1 to about 1.5 percent w/w, or about 0.3 to about 1.5 percent w/w, or about 1.0 percent w/w, of the composition.

C. Stabilizers

Compositions of the invention may optionally include one or more components that act as stabilizers. Stabilizers useful in the compositions are materials that aid in ensuring a stable composition and/or prevent growth of bacteria. Measures of stability include, e.g., maintenance of viscosity over time, maintenance of pH over time, or maintenance of appearance, homogeneity, and/or color over time. A stabilizer may be one or more of an antioxidant, a chelator, an antibacterial, or any other agent that acts to maintain desired characteristics of the composition over time. Suitable stabilizers include butylated hydroxyanisole (BHA), butylated hydroxytoluene (BHT), disodium edetate, methylparaben, butylparaben, propylparaben, benzyl alcohol, sorbic acid, imidurea, thimerisal, propyl gallate, sodium phosphate (monobasic and/or dibasic) and citric acid.

An example of an antioxidant for use in compositions of the invention is BHA, at about, e.g., 0.005 to about 0.1 percent w/w, or about 0.01 to about 0.05 percent w/w, or about 0.01 to 0.03 percent w/w, or about 0.02 percent w/w. Suitable chelating agents include ethylene diaminetetraacetic acid (EDTA), as EDTA disodium, calcium disodium edetate, EDTA trisodium, EDTA tetrasodium, or EDTA dipotassium. One or more chelating agents, e.g., EDTA disodium dihydrate, can optionally be included in the composition in amounts of about, e.g., 0.005 to about 1 percent w/w, or about 0.02 to about 0.2 percent w/w, or about 0.1 percent w/w. In some embodiments, a physiological buffer, for example, sodium phosphate, either monobasic or dibasic, or both, may be included in the composition as a stabilizer that acts as a buffer to stabilize pH over time. For the monobasic form, amounts may be, e.g., about 0.1 to about 1.5 percent w/w, or about 0.2 to about 1 percent w/w, or about 0.3 to about 0.7 percent w/w, or about 0.5 percent w/w. For the dibasic form, amounts may be, e.g., about 0.2 to about 2 percent w/w, or about 0.4 to about 1.5 percent w/w, or about 0.6 to about 1.2 percent w/w, or about 0.8%.

Other stabilizers may optionally be added to compositions of the invention; see, e.g., U.S. Pat. Nos. 6,013,270 and 6,390,291.

D. Water

The components of the composition are mixed with water to produce a composition of the desired viscosity. It is generally preferred to use water that has been purified by processes such as deionization or reverse osmosis, to improve the batch-to-batch formulation consistencies, by reducing or eliminating dissolved solids in the water supply. The amount of water in the composition will vary, depending on the amounts of the other components of the composition.

E. pH Modifier

The pH of the composition affects its potential for irritation of the bodily surface to which it is applied, as well as, in some embodiments, affecting the swelling of a thickener containing carboxyl groups by deprotonation of the carboxyl groups. If necessary, a pH modifier can be used to adjust the pH of the composition to a pH within a suitable range. A pH modifier is a compound that will adjust the pH of a composition to a lower, e.g., more acidic pH value, or to a higher, e.g., more basic pH value. Suitable pH modifiers include, for example, HCl, organic bases (such as triethanolamine) sodium hydroxide, potassium hydroxide, or ammonium hydroxide. In embodiments in which the thickening agent is a polyacrylate polymer, the pH modifier may be, for example, sodium hydroxide, to neutralize the polymer.

The composition may be at any pH that does not cause harm or irritation to the bodily surfaces to which the composition is applied in the intended manner and duration. Exemplary suitable pHs include, e.g., between about 6.0 to about 8.0, or between about 7.0 to about 7.7, or about 7.5.

F. Other Optional Ingredients

The compositions of the present invention may contain a wide range of additional, optional components. These depend on the intended use of the composition. For example, if the intended use includes cleansing the cul-de-sac of the eyes, the composition is preferably isotonic with respect to the fluids of the eye and sterile. A solution that is isotonic to the eye is characterized by osmolalities of about 270 to about 330 mOsm/kg. Osmolality of the solution of the invention may be adjusted by means of chlorides and/or bicarbonates of sodium or potassium, sodium lactate, dextrose, and mannitol. Compositions for use in the eye may optionally include other components that are naturally-occurring elements of the tear fluid, such as proteins, enzymes, lipids and metabolites. See, e.g., U.S. Pat. No. 4,911,933. Because the composition is applied to the eye, the composition should be sterile.

Other optional components of the composition that may be added, depending on the intended use, include, e.g., surfactants, naphthol soap (available commercially as FELS-NAPTHA™), a cooling agent, a fragrance component, a skin soothing or skin healing agent, and/or polyethylene granules to assist the composition in reaching irregularities of the skin (used, e.g., to assist in removal of irritating substances from the skin, such as urushiols from poison oak, ivy, and sumac). Surfactants include, e.g., sodium lauryl sarcosinate, sodium lauryl sulfate, nonoxynol 9, and other long-chain surfactants. Examples of cooling agents useful for the present invention include menthols, menthyl lactate, menthyl glycerol, menthyl salicylate, menthone glycerine acetal, alcohol, and borneols such as 1-menthol, dl-menthol, d-camphor, dl-camphor, d-borneol and dl-borneol. Plant extracts containing one or more of these compounds, for example, peppermint oil, peppermint extract, Perilla frutescens Britton var. acuta Kudo extract, camphor tree extract and lavender extract, may also be used. Examples of other useful cooling agents include asymmetrical carbonates, thiocarbonates and urethanes, N-substituted carboxamides, ureas or phosphine oxides, as described in *J. Cosmet. Chem.*, vol. 29, p. 185 (1978). These cooling agents may be used either singly or in any combination thereof. The cooling component is preferably incorporated into the composition in a proportion of from about 0.001, 0.005, 0.02, 0.05, 0.1, 0.5, 2, 3, 4, 5, 6, 7, 8, 9, or 10% by weight, to about 0.005, 0.02, 0.05, 0.1, 0.5, 2, 3, 4, 5, 6, 7, 8, 9, 10, 12 or 14% by weight. Cooling agents are further described in, e.g., U.S. Pat. Nos. 6,277,385 and 6,203,804. Fragrances are aromatic substances which can impart an aesthetically pleasing aroma to compositions of the invention. Typical fragrances include aromatic materials extracted from botanical sources (e.g., rose petals, gardenia blossoms, jasmine flowers, etc.) which can be used alone or in any combination to create essential oils. One or more fragrances can optionally be included in the composition in an amount ranging from about 0.001, 0.005, 0.02, 0.05, 0.1, 0.5, 2, 3, or 4% by weight to about 0.005, 0.02, 0.05, 0.1, 0.5, 2, 3, 4, or 5% by weight. Fragrance agents are further described in, e.g., U.S. Pat. No. 6,428,772. The compositions of the present invention may further comprise a skin soothing or skin healing component. Skin soothing or skin healing components suitable for use herein include, e.g., panthenoic acid derivatives (including, e.g., panthenol, dexpanthenol, ethyl panthenol), aloe vera, allantoin, bisabolol, and dipotassium glycyrrhizinate. The skin soothing or skin healing agent may be added to the present composition in a proportion from about 0.05, 0.1, 0.5, 2, 3, 4, 5, 7, 10, 15, 20, or 25% by weight to about 0.1, 0.5, 2, 3, 4, 5, 7, 10, 15, 20, 25, or 30% by weight. The CTFA Cosmetic Ingredient Handbook, Seventh Edition, 1997 and the Eighth Edition, 2000, describe a wide variety of other cosmetic and pharmaceutical ingredients commonly used in skin care compositions that are suitable for use in the compositions of the present invention. Examples of these functional classes disclosed in this reference include: absorbents, abrasives, anticaking agents, antifoaming agents, binders, biological additives, buffering agents, bulking agents, chemical additives, colorants, fragrance components, humectants, opacifying agents, plasticizers, propellants, reducing agents, skin-conditioning agents (emollient, humectants, miscellaneous, and occlusive), skin protectants, solubilizing agents, and suspending agents (nonsurfactant).

G. Combinations

Exemplary combinations of components for cleansing compositions include, for example, compositions containing polyethylene glycol, a thickening agent, and water, where the composition may contain, e.g., about 60 to about 99 percent w/w polyethylene glycol (PEG, e.g., PEG 300); about 0.1 to about 4 percent w/w polyacrylate thickening agent; and the balance water; where the composition is at a pH between about 6.0 and about 8.0. Another example of a combination that may be used in the invention is a combination containing about 84 to about 94 percent w/w PEG (e.g., PEG 300); about 0.1 to about 2 percent w/w polyacrylate thickening agent; and the balance water; where the composition is at a pH of about 7.0 to about 7.7. The latter composition may further contain stabilizer; for example, about 0.005 to about 0.05 percent w/w butylated hydroxyanisole; and about 0.05 to about 0.5 percent w/w EDTA/EDTA salts. In another embodiment, the composition may contain about 87 to about 91 percent w/w PEG (e.g., PEG 300); about 0.3 to about 1.5 percent w/w polyacrylate thickening agent; about 0.01 to about 0.03 percent w/w butylated hydroxyanisole; about 0.02 to about 0.2 percent w/w EDTA/EDTA salts; and about 9 to about 13 percent w/w water; where the composition is at a pH of about 7.0 to about 7.7. In a further embodiment, the composition may contain about 89.08 percent w/w PEG 300; about 1.0 percent w/w polyacrylate thickening agent; about 0.02 percent w/w butylated hydroxyanisole; about 0.1 percent w/w disodium edetate; and the balance water; where the composition is at a pH of about 7.5. In a further embodiment, the composition is about 87 to about 91 percent w/w PEG (e.g., PEG 300); about 0.3 to about 1.5 percent w/w polyacrylate thickening agent; about 0.01 to about 0.03 percent w/w butylated hydroxyanisole; about 0.02 to about 0.2 percent w/w EDTA/EDTA salts; and about 9 to about 13 percent w/w water; where the composition is at a pH of about 7.0 to about 7.7.

H. Containers and Packaging for the Composition

The composition may be provided in any suitable container known in the art or apparent to the ordinarily skilled artisan. Exemplary containers for the composition include towels or towellettes in which the composition is impregnated or dispersed, or containers holding the composition and from which the composition may be dispensed. Such containers may comprise elements for convenient dispensing of the composition, such as described in, e.g., U.S. Pat. No. 6,013,270. In some embodiments the composition may be provided impregnated in a porous substrate (e.g., towellette), such as described in, e.g., U.S. Pat. No. 6,015,763. The container may be further contained in suitable packaging.

In some embodiments of the invention the composition is provided in a container, and optionally further packaging, and a set of instructions for use of the composition to remove irritating substances, e.g., capsaicin, from the skin is also included. The instructions may be in any form, and provided, e.g., as a separate insert or on a label that is affixed to the container or packaging. Exemplary additional components include chemical-resistant disposal bags, applicators for applying the cleansing composition, towels or towellettes for the capsaicin cleansing lotion, diluent, gloves, eye protection, scissors, marking pens, and additional bodily surface-cleansing agents such as alcohol swabs.

II. Kits of the Invention

In an aspect, the present invention provides a kit including a composition comprising capsaicin (or capsaicin analog) and a composition in which capsaicin (or capsaicin analog) is soluble to at least about 10% w/w, or at least about 20% w/w, or at least about 25% w/w. In some embodiments, a kit of the invention include a capsaicin cleansing composition described above. Optionally, a third composition comprising an anesthetic may also be provided. The kits of the present invention may further comprise suitable packaging of the respective compositions, instructions, and/or other optional components as disclosed below.

A. Composition Comprising Capsaicin or a Capsaicin Analog.

The kits provided herein comprise a composition containing capsaicin or a capsaicin analog.

Capsaicin and its analogs are used both as irritants (e.g., pepper sprays) and in preparations for the relief of pain. Capsaicin selectively modulates sensory nerve fibers in such a way as to activate, then desensitize, nociceptors in peripheral tissues. Analogs of capsaicin with physiological properties similar to capsaicin may also be used in the kits provided herein; exemplary analogs of capsaicin are nonivamide, capsaicin isomers, and dihydrocapsaicin, described in, e.g., Govindarajan and Sathyanrayana, *Crit Rev Food Sci Nutr* 29:435-474 (1991); U.S. Pat. Nos. 5,290,816; 4,812,446; and 4,424,205; and Ton et al., *Brit J Pharmacol*, 10:175-182 (1955). Topical application of capsaicin and capsaicin analogs for pain relief is described in U.S. Pat. Nos. 6,239,180 and 6,248,788.

Kits of the invention may include a composition comprising capsaicin or a capsaicin analog in a wide variety of concentrations. These include, e.g., about 0.001 to about 60% by weight, for example, about 0.001 to about 1% by weight; or about 0.05% to about 15% by weight, or about 1% to about 10% by weight, or about 5% to about 10% by weight, or about 7.5% by weight. When supplied as a dermal patch (below), the capsaicin or capsaicin analog may be present at, e.g., about 0.01 mg/cm$^2$ to about 1 mg/cm$^2$, or about 0.1 to about 1 mg/cm$^2$, or about 0.3 to about 0.9 mg/cm$^2$, or about 0.64 mg/cm$^2$.

The capsaicin or capsaicin analog composition of the kits includes a vehicle suitable for topical or dermal application, for example (but not limited to) those described in U.S. Pat. Nos. 6,239,180 and 6,248,788. These patents disclose high concentration (e.g., >5% w/w) capsaicin or capsaicin analog compositions (including dermal patches) for topical applications, wherein the capsaicin may be in a vehicle such as a lotion, e.g. velvachol (available from Galderma USA) and EUCERIN™. In the case of a patch, the capsaicin is contained in a vehicle comprising a skin penetrating lotion or dispersed in a vehicle comprising a polymeric matrix, or mixed directly with a vehicle that also serves as adhesive for the patch. Other methods for the construction and uses of transdermal patches may be found in, e.g., *Drug Delivery Systems Characteristics and Biomedical Application*, R. L. Juiano, ed., Oxford University Press, N.Y. (1980); and *Controlled Drug Delivery*, Vol. I Basic Concepts, Stephen D. Bruck (1983).

The capsaicin or capsaicin analog and vehicle may be further packaged in any suitable packaging for segregation from other components of the kit and to facilitate dispensing of the composition.

B. Cleansing Composition.

The cleansing composition of the kits may be a composition in which capsaicin is soluble to at least about 10% w/w, or at least about 20% w/w, or at least about 25% w/w; e.g., any of the capsaicin cleansing compositions described herein. The composition may be provided in any suitable container, as described previously. The container may comprise elements for convenient dispensing of the cleansing composition, such as described in, e.g., U.S. Pat. No. 6,013,270. In some embodiments the cleansing composition may be provided impregnated in a porous substrate, such as described in, e.g., U.S. Pat. No. 6,015,763. The container may be further packaged in any suitable packaging for segregation from other components of the kit and to facilitate dispensing of the cleansing composition.

C. Anesthetic.

The kits of the invention may optionally further include an anesthetic composition. Burning pain and hyperalgesia to both heat and touch typically occur after applications of even the relatively low concentration capsaicin ointments known to the art. Such burning pain may be avoided by first administering an anesthetic, so as to cause regional anesthesia in the areas to be treated. Exemplary regional anesthetic agents that may be used in the anesthetic compositions optionally included in the kits of the invention are sodium channel blockers. A variety of sodium channel blocking anesthetics are known and useful, such as lidocaine, tetracaine, bupivicaine and chloroprocaine. The suitable anesthetic may be contained in a vehicle such as lotion or gel (see description for capsaicin compositions) or as a patch device (see description for capsaicin compositions). Anesthetics for use with capsaicin compositions are further described in U.S. Pat. Nos. 6,239,180 and 6,248,788.

The anesthetic and vehicle may be further packaged in any suitable packaging for segregation from other components of the kit and to facilitate dispensing of the composition.

D. Instructions.

Kits of the invention may further include instructions for use of the cleansing composition. Instructions may be included as a separate insert and/or as part of the packaging or container, e.g., as a label affixed to a container or as writing or other communication integrated as part of a container. The instructions may inform the user of methods for application and/or removal of the cleansing composition, precautions and methods concerning handling of material contaminated with an irritating or painful substance, expected results, warnings concerning improper use, and the like.

E. Additional Optional Components of the Kits of the Invention.

Kits of the present invention may further contain components useful in the application and removal of capsaicin or capsaicin analogs. Exemplary additional components include chemical-resistant disposal bags, applicators, bodily surface-cleansing agents such as alcohol swabs, diluent, towels or towellettes for wiping excess cream prior to the use of the capsaicin cleansing lotion and for wiping cleansing lotion, gloves, scissors, marking pens and eye protection.

III. Making Cleansing Lotions

One method for making some embodiments of the cleansing lotions provided by the present invention is shown in FIG. 1. PEG, water, and (if used) stabilizers such as BHA and/or EDTA and/or sodium phosphate, are combined in a manufacturing vessel and mixed until dissolved. The thickening agent, e.g., CARBOPOL 1382, is added to the mixture and dispersed, and mixing is continued until the polymer is properly hydrated. Then, if necessary, a pH modifier, e.g., 10% sodium hydroxide solution, is added and mixing is continued until a gel is formed.

IV. Methods of the Invention

The invention also provides methods for using the compositions and kits of the invention. In one embodiment, the invention provides a method for cleansing a bodily surface that has been contacted with an irritating or painful substance (e.g., capsaicin or a capsaicin analog, or a urushiol). Bodily surfaces to be treated may include skin, eyes, mucous membranes, hair, and, in the case of animals, fur (e.g., to cleanse an animal that has come into contact with an irritating, painful, or noxious substance). The bodily surface is cleansed by applying to the bodily surface a cleansing composition containing polyethylene glycol, a thickening agent, and water, then removing the composition from the bodily surface. Any of the compositions described herein may be used in the methods. In one embodiment, the cleansing composition may contain, e.g., about 80 to about 99 percent w/w polyethylene glycol; about 0.1 to about 2 percent w/w polyacrylate thickening agent; and about 1 to about 20 percent w/w water; where the composition is at a pH of about 7.0 to about 7.7. In another embodiment, the cleansing composition may contain about 87 to about 91 percent w/w polyethylene glycol; about 0.3 to about 1.5 percent w/w polyacrylate thickening agent; about 0.01 to about 0.03 percent w/w butylated hydroxyanisole; about 0.02 to about 0.2 percent w/w EDTA/EDTA salts; and about 9 to about 13 percent w/w water; where the composition is at a pH of about 7.0 to about 7.7; then removing the composition from the bodily surface.

Methods of the invention also include methods for treating an individual suffering from a capsaicin-responsive condition with the kits of the invention. For illustration and not limitation, capsaicin-responsive conditions include neuropathic pain (including pain associated with diabetic neuropathy, postherpetic neuralgia, HIV/AIDS, traumatic injury, complex regional pain syndrome, trigeminal neuralgia, erythromelalgia and phantom pain), pain produced by mixed nociceptive and/or neuropathic mixed etiologies (e.g., cancer, osteoarthritis, fibromyalgia and low back pain), inflammatory hyperalgesia, vulvar vestibulitis or vulvodynia, interstitial cystitis, neurogenic or overactive bladder, prostatic hyperplasia, rhinitis, rectal hypersensitivity, burning mouth syndrome, oral mucositis, herpes (or other viral infections), prostatic hypertrophy, dermatitis, pruritis, itch, tinnitus, psoriasis, warts, cancers (especially skin cancers), headaches, and wrinkles. As used herein, an "individual" is a vertebrate; e.g., a mammal; e.g., a human. The condition is treated by applying a composition comprising capsaicin or a capsaicin analog (as described above) to the area affected by the condition, then cleansing the area with a cleansing composition of the invention. The capsaicin may be administered in any number of ways, e.g., in a lotion, cream, emulsion, liniment, spray, transdermal patch, gel, or the like. The method may further include administering an anesthetic prior to the application of the capsaicin-containing composition, for example administering an afferent nerve fiber blocking regional anesthetic to the affected area. In one embodiment, the composition comprising capsaicin or a capsaicin analog may be contained in a transdermal patch. In such embodiments, the capsaicin cleansing composition may be used to cleanse areas around the patch after it has been affixed as well as any areas inadvertently exposed to capsaicin; in addition the capsaicin cleansing composition may be used to cleanse the area to which the patch was affixed, after removal of said patch. For cleansing the area after application of a patch and the removal of the patch, for example, a tube containing 50 gm of cleansing gel may be applied to a site following removal of capsaicin patch, e.g., an 8% capsaicin patch. The cleansing gel is left on the area for a period of time sufficient to allow capsaicin to be removed from the bodily surface to the gel, for example, for one minute, and then wiped off with dry gauze or dry paper towels. Upon removal from the treated area, all used gauze, paper towels or other materials placed in contact with the treated area are immediately disposed of in a plastic biohazard bag, which is then closed and sealed.

In some embodiments, the patch includes a reservoir containing a therapeutic formulation where the formulation is provided to the surface of the skin, and where the formulation comprises capsaicin or a capsaicin analog in a total concentration from greater than about 5% by weight of the formulation. In some embodiments, the capsaicin concentration is less than or equal to about 5% by weight of the composition.

V. Examples

Example 1

Several substances were evaluated for their ability to dissolve capsaicin. The solubility of capsaicin in different solvents was determined by exposing the sample to 90 minutes of sonication and allowing the water-bath temperature increase to approximately 40° C. Physical evaluation (i.e., visual) was conducted on the sample to determine solubility. The solubility of capsaicin in these substances is shown in Table 1.

TABLE 1

Solubility of capsaicin in various substances

| Solvent | Capsaicin Solubility (% w/w) |
|---|---|
| Mineral Oil | <1.0 |
| Isopropyl Myristate | <5.2 |
| Octyldodecanol | <5.2 |
| Peanut Oil | <3.6 |
| Soybean Oil | <3.5 |
| Oleyl Alcohol | 15.1-22.0 |
| Propylene Glycol | 23.4-26.3 |
| Ethanol, 95% | >50 |
| PEG 300 | 21.0-23.0 |
| Triacetin | 5.0-10.1 |
| Ethoxydiglycol | >50 |

The results of this Example show that capsaicin has a high solubility in PEG 300, which also has low irritation potential and is compatible with a variety of excipients.

Example 2

In this example, the solubility of capsaicin in three different forms of PEG and in PEG of different concentrations was tested. The mixtures were sonicated for two hours and allowed to reach ambient conditions. Samples were then centrifuged and filtered prior to being analyzed by HPLC.

The solubility of capsaicin in three different molecular weight PEGs, and in different concentrations of PEG 300 in water, is shown in Table 2.

TABLE 2

| Polyethylene Glycol | Capsaicin Solubility (% w/w) |
|---|---|
| PEG 200 | 27.0 |
| PEG 300 | 27.5 |
| PEG 400 | 22.0 |
| PEG 300/H$_2$O (80/20) | 12.5 |
| PEG 300/H$_2$O (90/10) | 27.0 |

Of the PEG's tested, PEG 300 has the greatest capacity for capsaicin, with a capsaicin solubility of 27.5% w/w. 90% PEG 300 has a greater solubility for capsaicin than 80% PEG 300 (27.0% vs. 12.5%, respectively). Capsaicin is also quite soluble in PEG 200, at 27%.

Example 3

In this example, formulations were prepared using various pH modifiers and with or without BHA and/or EDTA, or sodium phosphate, and their stabilities were followed over time at three different temperatures. Stability was assessed by evaluating appearance, pH, and viscosity. The formulations used are presented in Table 3.

TABLE 3

Formulations tested for stability

| Component | % (w/w) | | | | | | |
|---|---|---|---|---|---|---|---|
| | 43A | 43B | 44A | 44B | 45A | 54A | 54B |
| PEG 300 | 89.2 | 79.2 | 89.2 | 88.85 | 89.1 | 89.18 | 89.08 |
| CARBOPOL 1382 | 0.5 | 0.5 | 0.5 | 0.75 | 0.5 | 0.5 | 0.5 |
| Sodium Hydroxide | 0.03 | 0.03 | — | 0.04 | 0.03 | 0.03 | 0.03 |
| 50% Trolamine Soln. | — | — | 0.3 | — | — | — | — |
| BHA | — | — | — | — | 0.1 | 0.02 | 0.02 |
| Disodium Edetate | — | — | — | — | — | — | 0.1 |
| Purified Water qwad | 100 | 100 | 100 | 100 | 100 | 100 | 100 |

Stability data are presented in Table 4 (pH's are lower than the formulated pH's because the samples were diluted 1:9 with water). The method of preparation is shown in FIG. 1.

TABLE 4

Stability data for various formulations

| | | | Test | | | |
|---|---|---|---|---|---|---|
| | | | | | Viscosity | |
| Batch No.: | Storage Condition | Time | Appearance | pH (1:9) | cps | % From Initial |
| 790-43A | 5° C. | Initial | Clear - Slightly Hazy Gel | 5.3 | 5,000 | 100 |
| | | 2 Weeks | Conforms | 5.2 | N.T | — |
| | | 1 Month | Conforms | 5.2 | N.T | — |
| | | 3 Months | Conforms | N.T | N.T | — |
| | 25° | 2 Weeks | Conforms | 5.3 | N.T | — |
| | | 1 Month | Conforms | 5.2 | 5,300 | 110 |
| | | 3 Months | Conforms | 5.0 | 2,800 | 56 |
| | 40° | 2 Weeks | Conforms | 5.0 | 4,300 | 86 |
| | | 1 Month | Conforms | 4.9 | 2,600 | 52 |
| | | 2 Months | Conforms | N.T | 2,300 | 46 |
| | | 3 Months | Conforms | 4.5 | 2,400 | 48 |

TABLE 4-continued

Stability data for various formulations

| Batch No.: | Storage Condition | Time | Appearance | pH (1:9) | Viscosity cps | % From Initial |
|---|---|---|---|---|---|---|
| 790-43B | 5° C. | Initial | Clear - Slightly Hazy Gel | 5.1 | 6,700 | 100 |
| | | 2 Weeks | Conforms | 5.1 | N.T | — |
| | | 1 Month | Conforms | 5.2 | N.T | — |
| | | 3 Months | Conforms | N.T | N.T | — |
| | 25° | 2 Weeks | Conforms | 5.1 | N.T | — |
| | | 1 Month | Conforms | 5.0 | 5,500 | 82 |
| | | 3 Months | Conforms | 4.9 | 4,800 | 72 |
| | 40° | 2 Weeks | Conforms | 5.1 | 5,300 | 79 |
| | | 1 Month | Conforms | 4.9 | 2,900 | 43 |
| | | 2 Months | Conforms | N.T | 2,000 | 30 |
| | | 3 Months | Conforms | 4.2 | 1,800 | 27 |
| 790-44A | 5° C. | Initial | Clear - Slightly Hazy Gel | 5.6 | 3,600 | 100 |
| | | 2 Weeks | Conforms | 5.6 | N.T | — |
| | | 1 Month | Conforms | 5.5 | N.T | — |
| | | 3 Months | Conforms | N.T | N.T | — |
| | 25° | 2 Weeks | Conforms | 5.5 | N.T | — |
| | | 1 Month | Conforms | 5.5 | 3,500 | 97 |
| | | 3 Months | Conforms | 5.2 | 3,200 | 89 |
| | 40° | 2 Weeks | Conforms | 5.2 | 4,800 | 133 |
| | | 1 Month | Conforms | 5.3 | 3,000 | 83 |
| | | 2 Months | Conforms | N.T | 1,500 | 42 |
| | | 3 Months | Conforms | 4.7 | 1,700 | 47 |
| 790-44B | 5° C. | Initial | Clear - Slightly Hazy Gel | 5.2 | 10,600 | 100 |
| | | 2 Weeks | Conforms | 5.0 | N.T | — |
| | | 1 Month | Conforms | 5.0 | N.T | — |
| | | 3 Months | Conforms | N.T | N.T | — |
| | 25° | 2 Weeks | Conforms | 4.8 | N.T | — |
| | | 1 Month | Conforms | 5.0 | 9,300 | 88 |
| | | 3 Months | Conforms | 4.9 | 6,300 | 59 |
| | 40° | 2 Weeks | Conforms | 4.9 | 10,300 | 100 |
| | | 1 Month | Conforms | 4.7 | 7,500 | 71 |
| | | 2 Months | Conforms | N.T | 4,800 | 45 |
| | | 3 Months | Conforms | 4.2 | 5,300 | 50 |
| 790-45A | 5° C. | Initial | Clear - Slightly Hazy Gel | 5.2 | 4,300 | 100 |
| | | 2 Weeks | Conforms | 5.1 | N.T | — |
| | | 1 Month | Conforms | 5.1 | N.T | — |
| | | 3 Months | Conforms | N.T | N.T | — |
| | 25° | 2 Weeks | Conforms | 5.2 | N.T | — |
| | | 1 Month | Conforms | 5.1 | 4,900 | 114 |
| | | 3 Months | Conforms | 5.1 | 3,800 | 88 |
| | 40° | 2 Weeks | Conforms | 5.0 | 4,300 | 100 |
| | | 1 Month | Conforms | 4.9 | 4,100 | 95 |
| | | 2 Months | Conforms | N.T | 2,800 | 65 |
| | | 3 Months | Conforms | 4.7 | 2,300 | 53 |
| 790-54A | 5° C. | Initial | Clear - Slightly Hazy Gel | 5.3 | 6,500 | 100 |
| | | 2 Weeks | Conforms | N.T | N.T | — |
| | | 1 Month | Conforms | N.T | N.T | — |
| | | 3 Months | N.T | N.T | N.T | — |
| | 25° | 2 Weeks | Conforms | N.T | N.T | — |
| | | 1 Month | Conforms | 5.2 | 4,700 | 72 |
| | | 3 Months | Conforms | 5.2 | 5,000 | 77 |
| | 40° | 2 Weeks | Conforms | 5.2 | 6,800 | 105 |
| | | 1 Month | Conforms | 5.1 | 5,500 | 85 |
| | | 1.5 Months | Conforms | N.T | 5,500 | 85 |
| | | 3 Months | Conforms | 5.1 | 4,800 | 74 |

TABLE 4-continued

Stability data for various formulations

| Batch No.: | Storage Condition | Time | Appearance | pH (1:9) | Viscosity cps | % From Initial |
|---|---|---|---|---|---|---|
| 790-54B | 5° C. | Initial | Clear - Slightly Hazy Gel | 5.2 | 4,750 | 100 |
| | | 2 Weeks | Conforms | N.T | N.T | — |
| | | 1 Month | Conforms | N.T | N.T | — |
| | | 3 Months | N.T | N.T | N.T | — |
| | 25° | 2 Weeks | Conforms | N.T | N.T | — |
| | | 1 Month | Conforms | 4.9 | 4,700 | 99 |
| | | 3 Months | Conforms | 5.0 | 4,500 | 95 |
| | 40° | 2 Weeks | Conforms | 5.1 | 5,000 | 105 |
| | | 1 Month | Conforms | 5.1 | 4,250 | 89 |
| | | 1.5 Months | Conforms | N.T | 4,000 | 84 |
| | | 3 Months | N.T | N.T | N.T | — |

N.T. = not tested

This Example shows that several formulations are stable over time, especially those containing both BHA and EDTA, e.g., sample 790-54B.

Example 4

To determine the ability of cleansing gel to remove irritable substances from surfaces, a range of concentration of capsaicin solutions, in a volatile solvent, were applied to stainless steel coupons. Thin films of capsaicin (ranging from 4 μg to 16 μg per centimeter square) remaining on the surface of the steel coupons were equivalent to the maximum anticipated amount of capsaicin left on skin following clinical applications of 8% by weight capsaicin patches. The amount of cleansing gel used per square centimeter of surface, and application time were adapted from the clinical experience of cleansing gel usage.

Preparation of Capsaicin Solutions

A stock solution of capsaicin, in methanol, containing 103.1 mg/100 mL capsaicin ((Lot F0010103) Formosa Laboratories, Taiwan) in a 100-mL volumetric flask, was prepared. The solution was clear and colorless. 10 mL each of four concentrations of capsaicin solutions 0.4 mg/mL, 0.3 mg/mL, 0.2 mg/mL and 0.1 mg/mL were prepared from above stock solution.

Cleaning of Steel Coupons Exposed to Capsaicin Solutions

Four steel coupons, 5 cm×5 cm each, (316 SS Finish from Globe Pharma) were rinsed with methanol and allowed to dry completely. 1 mL of 0.1 mg/mL capsaicin solution was slowly applied to a coupon at about 40° C. (on a hot plate) such that methanol evaporated without solution dribbling from the edges.

For these experiments, a cleansing with the following components was used:

| Component | % (w/w) |
|---|---|
| Carbowax PEG 300 (Polyethylene Glycol 300) | 89.08 |
| Carbopol 1382 | 1.00 |
| Versene NA (Edetate Disodium) | 0.10 |
| Sodium Hydroxide, 10% solution | 0.30 |
| Butylated Hydroxyanisole | 0.02 |
| Purified Water | 9.50 |

The dried coupon was smeared with 1 mL of cleansing gel which was removed after one minute with a single pre-washed swab (which was also used to apply cleansing gel). The collected gel along with the swab was added to a pre-washed scintillation vial containing a small magnetic stirrer. 9 mL methanol was added and the sample was stirred for 10 minutes. Three more samples were prepared in similar fashion using 0.4 mg/mL, 0.3 mg/mL and 0.2 mg/mL capsaicin solutions. TABLE 5 describes the percent capsaicin recovery from four samples containing different initial capsaicin amounts.

TABLE 5

Percent Recovery of Capsaicin

| Sample ID (mg/mL) | UV Absorbance at 281 nm | Adjusted Absorbance[1] | Capsaicin Concentration of Recovered Solution[2] | Amount Capsaicin Recovered[3] (mg) | Amount Capsaicin Applied[4] (mg) | Percent Capsaicin Recovery |
|---|---|---|---|---|---|---|
| 0.10 | 0.212 | 0.156 | 0.011769 | 0.11769 | 0.1 | 117.7 |
| 0.20 | 0.261 | 0.205 | 0.016818 | 0.16818 | 0.2 | 84.1 |

TABLE 5-continued

Percent Recovery of Capsaicin

| Sample ID (mg/mL) | UV Absorbance at 281 nm | Adjusted Absorbance[1] | Capsaicin Concentration of Recovered Solution[2] | Amount Capsaicin Recovered[3] (mg) | Amount Capsaicin Applied[4] (mg) | Percent Capsaicin Recovery |
|---|---|---|---|---|---|---|
| 0.30 | 0.302 | 0.246 | 0.021042 | 0.21042 | 0.3 | 70.1 |
| 0.40 | 0.415 | 0.359 | 0.032684 | 0.32684 | 0.4 | 81.7 |

[1]Adjusted Abs. = Abs − subtraction factor (0.056)
[2]Concentration = (Adjusted Abs. − Y intercept)/slope [from linear curve in FIG. 2]
[3]Amount Recovered = Concentration × vol of solution containing recovered gel (i.e. 10 mL)
[4]Amount of capsaicin in one mL of application solution As the results in Table 3 indicate, the cleansing gel achieved an average of 88.4% capsaicin recovery. In the case of 0.1 mg/mL capsaicin concentration, experimental error appears to have led to a higher number (i.e. 117.7%). Exclusion of this data point shifts the average percent recovery down to 78.6% removal of residual amounts of capsaicin from an inert surface.

Example 5

This example describes the preparation of cleansing gels containing menthol as a cooling agent.

Cleansing gel formulations containing 1% L-menthol were prepared by combining 1.20 g of L-menthol (Spetram RL 1492) with 118.8 g of cleansing gel, mixing it overnight and additionally for 1 hour in a steam bath. The resulting formulation was a colorless gel with small amount of white solids, a characteristic odor of menthol, and a viscosity of 7,250 cps.

Cleansing gel formulations with 3% L-menthol were prepared by combining 3.61 g of L-menthol (Spetram RL 1492) with 116.41 g of cleansing gel, mixing it overnight and additionally for 1 hour in a steam bath. The resulting formulation was a colorless gel with medium amount of white solids, a characteristic odor of menthol, and a viscosity of 6,500 cps.

Cleansing gel formulations with 10% L-menthol were prepared by combining 1.20 g of L-menthol (Spetram RL 1492) with 118.8 g of cleansing gel, mixing it overnight and additionally for 1 hour in a steam bath. The resulting formulation was a colorless gel with white solids, a characteristic odor of menthol, and a viscosity of 4,750 cps.

Example 6

This example describes the lack of skin penetration of polyethylene glycols that make up PEG 300.

PEG 300 is a polymer of ethylene glycol. The molecular weight of polymers is reported as an average of all constituting fractions. PEG has an average molecular weight of 300. PEG 300 was analyzed to detect and estimate polymer units with 5 to 8 monomer units the molecular weights of which constitute a range centered on 300 (i.e. PEG 239, PEG 283, PEG 327, and PEG 371). As expected these molecules were abundant in the cleansing compositions provided by the present invention, as determined by LC-MS, and were used as representative molecules in this Example.

The cleansing gel described in Example 4 was placed on human cadaver skin that was mounted on an O-ring and placed between the donor and receiver chambers of a Franz diffusion cell. The penetration of the four components across the skin was investigated over a three-hour period. These results were compared to those for caffeine, a reference compound for high permeation, and atenolol, a reference compound for low permeation. Table 6 provides the skin permeability coefficients (Papp) for the monitored components of the cleansing gel composition and the two reference compounds. Donor #1 was untreated skin. Donor #2 was skin treated with an 8% capsaicin composition for 60 minutes.

TABLE 6

Permeability of skin to PEG, caffeine, and atenolol

| | Papp (cm/hr) | |
|---|---|---|
| Compound | Donor #1 | Donor #2 |
| PEG 239 | $0.5 \times 10^{-7}$ | $2.8 \times 10^{-7}$ |
| PEG 283 | $0.5 \times 10^{-7}$ | $2.0 \times 10^{-7}$ |
| PEG 327 | $0.5 \times 10^{-7}$ | $1.9 \times 10^{-7}$ |
| PEG 371 | $0.5 \times 10^{-7}$ | $1.5 \times 10^{-7}$ |
| Caffeine | $3.0 \times 10^{-4}$ | $5.1 \times 10^{-4}$ |
| Atenolol | $1.9 \times 10^{-5}$ | $3.6 \times 10^{-5}$ |

The Papp of each of the four main components of the cleansing gel was significantly lower than the low permeability reference, indicating that the permeability of skin to the polyethylene glycol components of the cleansing gel is exceptionally low, e.g., having a Papp of not greater than $1 \times 10^{-6}$, or $5 \times 10^{-7}$ cm/hr.

It is understood that the examples and embodiments described herein are for illustrative purposes only and that various modifications or changes in light thereof will be suggested to persons skilled in the art and are to be included within the spirit and purview of this application and scope of the appended claims. All publications, patents and patent applications cited herein are hereby incorporated by reference in their entirety for all purposes to the same extent as if each individual publication, patent or patent application were specifically and individually indicated to be so incorporated by reference.

The invention claimed is:

1. A kit comprising:
 a) a first composition comprising capsaicin or a capsaicin analog; and
 b) a second composition for cleansing capsaicin from a bodily surface comprising:
  i) about 80 to about 99 percent w/w polyethylene glycol (PEG); and
  ii) about 0.1 to about 4.0 percent w/w polyacrylate thickening agent, wherein the second composition is aqueous and has a viscosity of between 100 to 8000 cps.

2. The kit of claim 1, wherein the second composition comprises about 84 to about 94 percent w/w polyethylene glycol (PEG).

3. The kit of claim 2, wherein the second composition further comprises a stabilizer.

4. The kit of claim 3, wherein the second composition further comprises a cooling agent.

5. The kit of claim 3, wherein the second composition comprises:
   a) about 87 to about 91 percent w/w polyethylene glycol (PEG);
   b) about 0.3 to about 2 percent w/w polyacrylate thickening agent;
   c) about 0.01 to about 0.03 percent w/w butylated hydroxyanisole;
   d) about 0.02 to about 0.2 percent w/w edetate sodium; and
   e) the balance water;
   wherein the second composition is at a pH of about 7.0 to about 7.7.

6. The kit of claim 5, wherein the second composition comprises:
   a) about 89.08 percent w/w PEG 300;
   b) about 1.0 percent w/w polyacrylate thickening agent;
   c) about 0.02 percent w/w butylated hydroxyanisole;
   d) about 0.1 percent w/w disodium edetate; and
   e) the balance water;
   wherein the second composition is at a pH of about 7.5.

7. The kit of claim 1, wherein the second composition has a pH between about 7.0 and about 7.7.

8. The kit of claim 1, wherein the second composition comprises about 90 percent w/w polyethylene glycol (PEG).

9. The kit of claim 8, wherein the second composition further comprises:
   a) about 0.1 to about 2.0 percent w/w polyacrylate thickening agent; and
   b) the balance water;

wherein the second composition is at a pH between about 7.0 and about 7.7.

10. The kit of claim 1, wherein the PEG of the second composition is PEG 200 to PEG 600.

11. The kit of claim 1, wherein capsaicin has a solubility of at least about 10 to 25 percent w/w in the second composition.

12. The kit of claim 11, wherein capsaicin has a solubility of about 10 percent w/w in the second composition.

13. The kit of claim 11, wherein capsaicin has a solubility of about 20 percent w/w in the second composition.

14. The kit of claim 11, wherein capsaicin has a solubility of about 25 percent w/w in the second composition.

15. The kit of claim 1, wherein the second composition is a surfactant-free gel.

16. The kit of claim 1, wherein the viscosity of the second composition is between 4000 cps to 8000 cps.

17. The kit of claim 16, wherein the viscosity of the second composition is between 4000 to 5000 cps.

18. The kit of claim 1, wherein the viscosity of the second composition is between 2000 to 5000 cps.

19. The kit of claim 1, wherein the viscosity of the second composition is between 100 to 1000 cps.

20. The kit of claim 1, wherein the second composition is substantially free of particulates.

21. The kit of claim 1, wherein the polyacrylate thickening agent of the second composition is an acrylic acid/ethylacrylate copolymer or a carboxyvinyl polymer.

22. The kit of claim 1, wherein the first composition comprises the capsaicin or the capsaicin analog contained in a transdermal patch.

23. The kit of claim 22, wherein the capsaicin or the capsaicin analog is present in the transdermal patch at an amount of about 0.64 mg/cm$^2$.

24. The kit of claim 22, wherein the capsaicin or the capsaicin analog is present in the transdermal patch in an amount of about 5% to about 10% by weight.

* * * * *